United States Patent [19]

Rink et al.

[11] 4,369,179

[45] Jan. 18, 1983

[54] ACYLPEPTIDES

[75] Inventors: Hans Rink, Riehen; Peter Sieber, Reinach; Bruno Kamber, Arlesheim, all of Switzerland

[73] Assignee: Ciba-Geigy Corporation, Ardsley, N.Y.

[21] Appl. No.: 213,299

[22] Filed: Dec. 5, 1980

[30] Foreign Application Priority Data

Dec. 14, 1979 [CH] Switzerland .................. 11096/79

[51] Int. Cl.³ .................. A61K 37/00; C07C 103/52
[52] U.S. Cl. .................. 424/177; 260/112.5 S
[58] Field of Search .................. 260/112.5 S; 424/177

[56] References Cited

U.S. PATENT DOCUMENTS

| | | | |
|---|---|---|---|
| 3,725,380 | 4/1973 | Konig et al. | |
| 3,794,633 | 2/1974 | Kamber et al. | |
| 3,862,113 | 1/1975 | Riniker et al. | |
| 3,872,074 | 3/1975 | Konig et al. | |
| 3,875,207 | 4/1975 | Iselin et al. | |
| 3,944,590 | 3/1976 | Iselin et al. | |
| 3,988,304 | 10/1976 | Garsky | 260/112.5 S |
| 4,000,259 | 12/1976 | Garsky | 260/112.5 S |
| 4,062,816 | 12/1977 | Shields | 260/112.5 S |
| 4,098,782 | 7/1978 | Sarantakis | 260/112.5 S |
| 4,115,554 | 9/1978 | Veber | 260/112.5 S |
| 4,140,767 | 2/1979 | Veber | 260/112.5 S |
| 4,191,754 | 3/1980 | Veber et al. | 260/112.5 S |
| 4,235,886 | 11/1980 | Freidinger et al. | 260/112.5 S |
| 4,238,481 | 12/1980 | Rink et al. | |

OTHER PUBLICATIONS

Pettit, Synthetic Peptides, vol. I, pp. 52, 53.
Science 179, 77(1973).
K. Lübke, E. Schröder & G. Kloss: Chemie U. Biochemie der Aminosäuren, Peptide U. Proteine I (G. Thieme Verlag, 1975), p. 304.
J. Rivier et al.: *Peptides* 1976; Proceedings of the Fourteenth European Peptide Symposium, Wepion, Belgium, Apr. 11–17; pp. 427–451.
A. P. Hansen & K. Lundbaeck: Diabete et Metabolisme [Paris] (1976) 2, 203–218.
W. Vale, J. Rivier et al.: Metabolism, vol. 27, No. 9, Suppl. 1, (Sep. 1978), 1391–1491.
D. F. Veber et al.: Nature, vol. 280, 512–514 (Aug. 9, 1979).

*Primary Examiner*—Delbert R. Phillips
*Attorney, Agent, or Firm*—Norbert Gruenfeld; Prabodh I. Almaula

[57] ABSTRACT

Acylpeptides derived from somatostatin or from a derivative thereof having analogous action, in which the amino acids sequence is modified by omitting individual amino acids and/or by exchanging them for other amino acids, and in which the $\epsilon$-amino group of the lysine residue in the 9-position, and optionally also the $\epsilon$-amino group of the lysine residue in the 4-position and/or the N-terminal $\alpha$-amino group carries the acyl radical of an optionally substituted alkanecarboxylic acid, and salts and complexes thereof can be used as antidiabetics and/or for combating gastrointestinal bleeding. They are manufactured by conventional methods of peptide chemistry.

18 Claims, No Drawings

ACYLPEPTIDES

The invention relates to novel acylpeptides derived from somatostatin and its analogues, processes for the manufacture of these acylpeptides, pharmaceutical preparations containing the same and the use of these compounds and preparations for therapeutic purposes.

The acylpeptides according to the invention are derivatives of somatostatin and of analogues derived therefrom, in which the ε-amino group of the lysine residue in the 9-position, and optionally also the ε-amino group of the lysine residue in the 4-position and/or the N-terminal amino group is substituted by the radical of a carboxylic acid, it being possible to modify the amino acids sequence of somatostatin by omitting individual amino acids or by exchanging them for other amino acids.

As is known, somatostatin, a cyclic tetradecapeptide of the formula

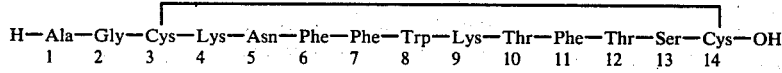

[Science 179, 77 (1973)], inhibits the pituitary-controlled secretion of the somatotrophic hormone (somatotrophin). It also inhibits the secretory activity of the endocrine pancreas, such as the secretion of insulin and glucagon. In the case of somatostatin itself, these valuable properties cannot be used fully in practice since this compound has too short a duration of action. In addition, it is often preferable for the active substance to exercise its inhibitory effect predominantly on one of the hormones mentioned. For this reason, attempts are being made to achieve a dissociation of the inhibitory effects and a duration of action which is as long as possible by modifying the basic sequence, especially by omitting individual original amino acids and/or exchanging them for other, often "unnatural", amino acids.

Surprisingly, it has now been found that, by a very unusual modification of the basic structure, which comprises acylating the ε-amino group of the lysine residue in the 9-position of somatostatin or a structural analogue thereof having a similar action with an optionally substituted alkanecarboxylic acid, an acylpeptide is produced in which the original activity of the basic structure is not only maintained but often increased and heightened still further in the sense discussed above, especially in respect of the duration of action. Such a result is all the more surprising in view of the fact that the basic character of the terminal amino group of the Lys$^9$ residue, which is considered indispensable for the biological action of somatostatin and analogous active substances, is thereby eliminated.

The compounds according to the invention are often advantageous also from the technical standpoint since, in their synthesis from smaller building blocks, the selective protection of the amino groups concerned, specifically the ε-amino groups of lysine residues, is no longer necessary and hence the synthesis is simplified.

From this point of view, of the acylpeptides of the invention in general, and also of their representatives which are given special emphasis hereinbelow, there are preferred those in which all the amino groups concerned carry the same acyl radical.

The present invention relates especially to acylpeptides derived from somatostatin and analogues thereof, having the general formula

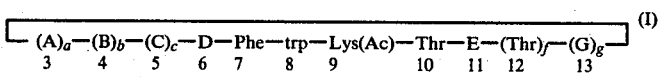

in which

Ac represents an acyl radical of an optionally substituted alkanecarboxylic acid, present at the free amino group, A represents the radical of the partial formula

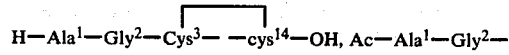

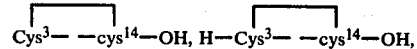

(wherein cys represents L-Cys or D-Cys and Bmp represents the desaminocysteine residue), or the residue of an ω-amino-lower alkanecarboxylic acid of the partial formula —NH—CH(R)—(CH$_2$)$_n$—CO— (wherein n represents 0 or an integer from 1 to 6 and R represents hydrogen or carboxyl) which, if n=2 and R is hydrogen, can also be substituted by a cyclic hydrocarbyl radical and, in that case, is designated hereinafter as Gaba(Ar), B represents Lys, Lys(Ac) or Lys(X) (wherein X is an ε-amino-protecting group), C represents Asn, Ala or His, D represents Phe or, if no sulphur-containing amino acid residues are present in the radical A, together with E may represent the radical

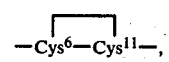

trp represents L-Trp, D-Trp or an analogous radical, which carries in the indole nucleus, for example in the 5-position, a halogen atom, especially fluorine, E represents Phe or Tyr or, together with D, has the meaning given above.

G represents L-Ser, D-Ser or the residue of a secondary α-amino acid having a maximum of 8 carbon atoms, and a, b, c, f and g each represents, independently of one another, 0 or 1, and non-toxic salts and pharmacologically acceptable complexes thereof.

The alkanecarboxylic acid forming the basis of the acyl radical Ac has preferably not more than 18 carbon atoms if it is unsubstituted and preferably not more than 8 carbon atoms if it is substituted. The substituents are, on the one hand, hydroxyl, mercapto, lower alkylthio, such as methylthio, guanidino, carboxyl, carboxamido and especially primary amino groups, or an imino group bonded at two different carbon atoms, and, on the other hand, mono- or bicyclic hydrocarbyl or heterocyclyl radicals, such as especially phenyl, p-hydroxyphenyl, 1- or 2-naphthyl, 2-, 3- or 4-pyridyl, 2- or 3-indolyl, 2- or 4-imidazolyl, 2-, 4- or 5-thiazolyl, 2-thienyl or 2-furyl. The acid may carry one or more substituents of the same kind or different kinds, the total number of carbon atoms, including the carbon-containing substituents, being preferably not more than 18. Especially preferred are acyl radicals that are derived from singly branched or especially straight-chained unsubstituted alkane-(mono or di)-carboxylic acids, the former having a maximum of 18, and the latter a maximum of 9, carbon atoms, such as those derived from acetic, propionic, butyric, isobutyric, valeric, isovaleric, caproic, oenanthic, undecanoic, lauric, myristic, palmitic and stearic acid on the one hand, and malonic, succinic, glutaric, adipic, pimelic and suberic acid on the other hand.

Especially preferred are also acyl radicals that are derived from α-amino acids of the L-series which are naturally occurring, especially as peptide building blocks, and their closely related analogues, such as, especially, the enantiomers of the "unnatural" D-series. Of the preferred α-amino acids, for example the following are most especially suitable: glycine, alanine, valine, leucine, isoleucine, phenylalanine, aspartic acid, glutamic acid, arginine, lysine and histidine, also β-alanine, α-aminobutyric acid, γ-aminobutyric acid, norvaline, isovaline, norleucine and ornithine, and also asparagine, glutamine, tyrosine, tryptophan, methionine, threonine, serine, and, most especially, proline and hydroxyproline in which the α-amino group is cyclised with the alkyl radical to form a ring.

The ε-amino-protecting group of the Lys⁴ residue denoted by the symbol X has the meanings given hereinbelow. It differs fundamentally from the above-characterised acyl group Ac in that it can be split off selectively with the amino group being liberated, whereas the acyl group Ac of the ε-amino group cannot be detached without at the same time impairing the peptidic amide bonds.

The radical denoted Gaba(Ar) is more precisely defined by the formula

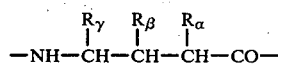

in which one of the symbols $R_\alpha$, $R_\beta$ and $R_\gamma$ is an unsubstituted or substituted cyclic hydrocarbyl radical Ar and the other two represent hydrogen. The substituted γ-aminobutyric acid corresponding to the radical Gaba-(Ar) has the short form H—Gaba(Ar)—OH.

the cyclic hydrocarbyl radical Ar is a mono-, di- or polycyclic cycloalkyl radical or a corresponding aryl radical containing at least one aromatic ring and having a maximum of 18, preferably a maximum of 12, ring carbon atoms. Of the cycloalkyl radicals, those that are preferred have 3- to 8-membered, and especially 5- and/or 6-membered, rings, such as, for example, cyclopropyl, cyclobutyl, cycloheptyl, cyclooctyl and more especially cyclopentyl and cyclohexyl, also 1-bicyclo[2,2,2]-octyl, 2-bicyclo[2,2,2]octyl, 2-bicyclo[2,2,1]heptyl, 1- or 2-adamantyl, and 1- or 2-perhydronaphthyl, i.e. bicyclo[4,4,0]decyl. An aryl radical is especially a naphthyl radical, such as 1- or 2-naphthyl, a corresponding partially hydrogenated naphthyl radical, such as, especially, 1-, 2-, 5- or 6-(1,2,3,4-tetrahydronaphthyl), phenyl, anthryl, fluorenyl or azulenyl. All of these cyclic hydrocarbyl radicals may carry one or more lower aliphatic hydrocarbyl radicals, especially alkyl radicals having a maximum of 4 carbon atoms, for example methyl, ethyl, propyl, isopropyl or butyl, and/or further cyclic, especially monocyclic, hydrocarbyl radicals, such as those defined above, the total number of carbon atoms being a maximum of 18. Examples of such cyclic hydrocarbyl radicals are 4,4-dimethylcyclohexyl, tolyl, such as 2-, 3- or 4-tolyl, and biphenylyl, for example 4-biphenylyl.

The aromatic moiety of the cyclic hydrocarbyl radicals may be substituted by one, two or more identical or different substituents, such as halogen, for example chlorine, bromine, iodine and especially fluorine, phenoxy, lower alkoxy, for example one derived from one of the above-mentioned lower alkyl radicals having a maximum of 4 carbon atoms, including, especially, methoxy, also nitro and amino, especially primary amino, di-lower alkylamino and acylamino, such as lower alkanoylamino, for example acetamino. Especially preferred are phenyl radicals substituted by the mentioned substituents.

The radical Ar is found in the α-, γ- or preferably the β-position of the chain of γ-aminobutyric acid; accordingly, especially preferred radicals of the formula Gaba-(Ar) are derived from the following butyric acids: 4-amino-3-phenyl-, 4-amino-3-cyclohexyl-, 4-amino-3-(2-naphthyl)- and especially 4-amino-3-(1-naphthyl)- butyric acid and 4-amino-3-(3-phenoxyphenyl)-butyric acid.

The secondary α-amino acid having a maximum of 8 carbon atoms mentioned in the symbol G is an α-lower alkylamino-lower alkylcarboxylic acid in which the two lower alkyl radicals may be connected to each other by a C-C bond, an oxygen atom, a sulphur(II) atom or an optionally lower alkylated nitrogen atom, each individual lower alkyl radical containing a maximum of 6 carbon atoms and both together containing a maximum of 7 carbon atoms. The lower alkyl radical forming the basis of the carbon skeleton of the carboxylic acid has preferably more than one carbon atom and is especially one that occurs in natural amino acids, such as butyl, isobutyl, pentyl and especially ethyl or isopentyl. The lower alkyl radical that occurs as a substituent of the amino group or the nitrogen bridge is preferably methyl. The C-C bond which optionally connects the two lower alkyl radicals is preferably a single bond. The α-amino group is preferably in a steric configuration that corresponds to the natural amino acids, i.e. the L-amino acids. Preferred radicals of such secondary α-amino acids are especially those that are known as naturally occurring amino acids, such as, especially, L-proline, or those that are directly analogous to these in structure, such as, on the one hand, 4-oxaproline and especially 4-thiaproline of the formula

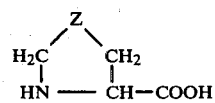

in which Z is oxygen or sulphur, and, on the other hand, an N-lower alkylated, especially N-methylated, aliphatic amino acid, especially N-methyl-L-leucine.

Of the acylpeptides according to the invention, there should be emphasised those which are derived from especially valuable somatostatin-like basic peptides known per se and are characterised by specific formulae, such as those given below:

Thus somatostatin, D-Trp$^8$-somatostatin, [D-Trp$^8$-D-Cys$^{14}$-]-somatostatin, [(5-F)-D-Trp$^8$]-somatostatin and des-[Ala$^1$-Gly$^2$]-somatostatin form the basis of acylpeptides of the following formula IA:

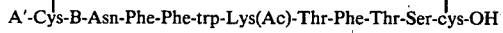

(IA)

A'-Cys-B-Asn-Phe-Phe-trp-Lys(Ac)-Thr-Phe-Thr-Ser-cys-OH in which A' represents Ala-Gly-, Ac-Ala-Gly-, H- or Ac- and Ac, B, trp and cys have the meanings given at the beginning; derived from des-[Ala$^1$-Gly$^2$-]-desamino-Cys$^3$-somatostatin and its structural analogues are the acylpeptides of the formula IB:

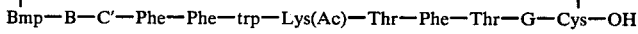

(IB)

Bmp—B—C'—Phe—Phe—trp—Lys(Ac)—Thr—Phe—Thr—G—Cys—OH in which Ac, Bmp, B, trp and G have the meanings mentioned at the beginning and C' represents Asn or His; derived from oligopeptides in which one or more of the amino acids in the positions 1, 2, 4, 5, 12 and 13 of [D-Trp$^8$]-somatostatin or [D-Trp$^8$-D-Cys$^{14}$]-somastatin are omitted, are acylpeptides of the formula IC:

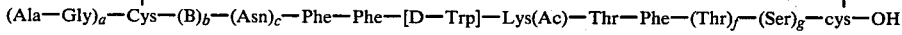

(IC)

(Ala—Gly)$_a$—Cys—(B)$_b$—(Asn)$_c$—Phe—Phe—[D—Trp]—Lys(Ac)—Thr—Phe—(Thr)$_f$—(Ser)$_g$—cys—OH in which Ac, B and cys have the meanings mentioned at the beginning and a, b, c, f and g each represents, independently of one another, 0 or 1; derived from analogues having the (6–11)-cystine bridge are the bicyclic acylpeptides of the formula I in which A represents the residue of ω-aminoheptanoic acid, D and E together represent the radical

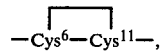

—Cys$^6$—Cys$^{11}$—, a represents 1 and b, c, f and g represent 0, and which correspond to the formula ID:

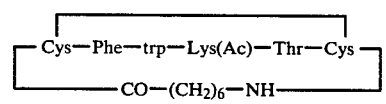

(ID)

—Cys—Phe—trp—Lys(Ac)—Thr—Cys—
—CO—(CH$_2$)$_6$—NH— in which Ac and trp have the meanings mentioned at the beginning; and finally sulphur-free cyclopeptides having partial sequences of at least 6 and not more than 11 of the amino acids of the somatostatin ring form the basis of the acylpeptides of the formula IE:

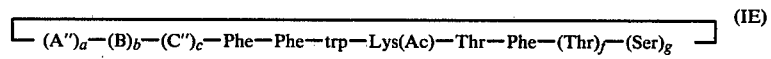

(IE)

(A")$_a$—(B)$_b$—(C")$_c$—Phe—Phe—trp—Lys(Ac)—Thr—Phe—(Thr)$_f$—(Ser)$_g$ in which a, b, c, f and g each represents, independently of one another, 0 or 1, Ac, trp and B have the meanings mentioned at the beginning. A" denotes the radical —NH—CH(R)—(CH$_2$)$_n$—CO— or Gaba(Ar) characterised at the beginning and C" represents Asn or Ala.

Especially preferred acylpeptides of the formula IE are those in which Ac has the general and especially emphasised meanings defined at the beginning, trp represents D-Trp, A" denotes an ω-amino-lower alkanecarboxylic acid residue, in which R represents hydrogen and n represents 0 or an integer from 1 to 3, B represents Lys, Lys(Ac) or Lys(INOC) (wherein INOC denotes the isonicotinyloxycarbonyl present at the ε-amino group), f and at least one of the symbols a, b, c and g are equal to 1, whilst the others each represent, independently of one another, 0 or 1, such as especially those compounds in which a=0 and b, c, f, g=1 or a, b=0 and c, f, g=1 or a, b, c=0 and f, g=1 or alternatively a, b, g=0 and c, f=1.

Most especially preferred acylpeptides of the formula IE are those in which Ac has the general and especially emphasised meanings defined at the beginning, trp represents D-Trp, A" represents the radical Gaba(Ar) defined at the beginning, especially one having the hydrocarbyl Ar in the β-position, or an ω-amino-lower alkylcarboxylic acid residue in which n represents 0 or an integer from 1 to 6, especially from 1 to 3, and more especially 2, and R represents carboxyl and especially hydrogen, C" represents Ala and especially Asn, a equals 1, c equals 0 or especially 1 and b, f and g equal 0. Of these, there should be especially emphasised compounds in which, in the radical A", n=5 and R represents hydrogen or carboxyl, a=1 and b, c, f and g all equal 0, and especially compounds of the formula

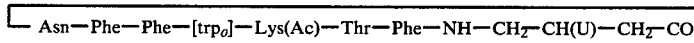

(IF)

Asn—Phe—Phe—[trp$_o$]—Lys(Ac)—Thr—Phe—NH—CH$_2$—CH(U)—CH$_2$—CO in which trp$_o$ represents D-Trp which may also carry fluorine in the 5-position, Ac has the general and especially emphasised meanings defined at the beginning and U represents hydrogen or the radical Ar defined at the beginning, especially the phenyl, cyclohexyl, 2-naphthyl and especially 1-naphthyl or m-phenoxyphenyl radical.

As a result of substitution with the radical Ar a centre of asymmetry is produced at the β-carbon atom of the γ-aminobutyric acid which results in the presence of in each case two diastereoisomeric forms of the cyclopeptide according to the invention which may, if desired, be used separately or, alternatively, together, as a mixture of diastereoisomers, for the same purposes.

Most especially preferred are acylpeptides of the above formulae I to IF, in which Ac represents an acyl radical according to the examples of carrying out the process, or which have the basic structure of one of the acylpeptides shown in the Examples. The acylpeptides shown in the Examples are then most of all preferred.

Those acylpeptides of the formula I containing a free carboxyl group which are characterised above either in general terms or as being preferred may alternatively be in the form of salts, for example sodium, potassium, calcium or magnesium salts, or alternatively in the form of ammonium salts derived from ammonia or a physiologically tolerable organic nitrogen-containing base. Those acylpeptides of the formula I containing a free amino group which are characterised above either in general terms or as being preferred may alternatively be in the form of their salts, that is their acid addition salts. Suitable acid addition salts are especially physiologically tolerable salts with conventional therapeutically acceptable acids; of the inorganic acids, mention should be made of hydrohalic acids, such as hydrochloric acid, and also of sulphuric acid and phosphoric or pyrophosphoric acid; of the organic acids, mention should be made especially of sulphonic acids, for example benzenesulphonic acid and p-toluenesulphonic acid, or of lower alkanesulphonic acids, such as methanesulphonic acid, also of carboxylic acids, such as acetic acid, lactic acid, palmitic and stearic acid, malic acid, tartaric acid, ascorbic acid and citric acid.

The acylpeptides of the formula I according to the invention may alternatively be in the form of complexes. Complexes should be understood as being compounds the structures of which have not yet been fully clarified and that are formed when certain inorganic or organic substances are added to peptides and that impart to these a prolonged action. Such substances are described, for example, for ACTH and other adrenocorticotropically active peptides. Those that should be mentioned are, for example, inorganic compounds that are derived from metals, such as calcium, magnesium, aluminium, cobalt and especially zinc, especially sparingly soluble salts, such as phosphates, pyrophosphates and polyphosphates, as well as hydroxides of these metals, also alkali metal polyphosphates, for example Calgon ®N, Calgon ®322, Calgon ®188 or Polyron ®B 12. Organic substances that prolong action are, for example, non-antigenic types of gelatin, for example polyoxygelatin, polyvinylpyrrolidone and carboxymethylcellulose, also sulphonic or phosphoric acid esters of alginic acid, dextran, polyphenols and polyalcohols, especially polyphloretin phosphate and phytic acid, andalso polymers and copolymers of basic or, especially, acidic, amino acids, for example protamine or polyglutamic acid.

Unless otherwise indicated, the short forms of the amino acid residues refer to residues of the α-amino acids of the L-series that occur naturally.

Unless otherwise indicated, the term "lower" wherever it occurs in connection with an organic radical or a compound, indicates such a radical or compound having a maximum of 7 carbon atoms and preferably a maximum of 4 carbon atoms.

The novel acylpeptides according to the invention have a physiological action that is fundamentally similar to the action of somatostatin. They can therefore be used advantageously in therapeutic indications similar to those of somatostatin, for example especially for the treatment of functional disorders in which the secretion of the somatotrophic hormone or glucagon is abnormally high, such as in the case of acromegaly or diabetes. Since they also inhibit blood losses in the gastrointestinal tract they can also be used successfully in this area of indication. They can also be used as valuable intermediates for the manufacture of other therapeutically valuable compounds, for example those having a further modified acyl radical Ac.

The acylpeptides according to the invention are obtained by using conventional manufacturing processes of peptide chemistry which are known per se.

Thus, they are manufactured, for example, by acylating a corresponding peptide having a free ε-amino group of the lysine residue in the 9-position, optionally while temporarily protecting any free hydroxyl groups and/or other free amino groups. The acylation is effected especially by treating a peptide of the formula

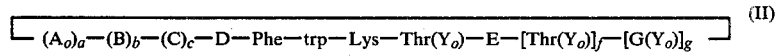
(II)

in which $A_o$ represents a radical corresponding to the radical A defined at the beginning in which the α-amino group of an N-terminal amino acid residue may carry an α-amino-protecting group X′ having the meaning defined in detail below, $Y_o$ represents a hydrogen atom present at the oxygen atom, or a hydroxyl-protecting group Y having the meaning defined in detail below, and in which the other symbols have the meanings given at the beginning, with an alkanecarboxylic acid $Ac_oOH$, in which $Ac_o$ represents a radical corresponding to the acyl radical Ac defined at the beginning in which any amino and hydroxyl groups present may carry protecting groups X and X′, and Y respectively, or with a reactive derivative of such an acid and, if desired or necessary, liberating the amino groups and hydroxyl groups in the resulting product by splitting off the protecting groups X and X′, and Y respectively.

The above-mentioned residue of an N-terminal amino acid does not occur in all meanings of A or $A_o$ but only in those that are indicated by the symbol A′, and is represented by the radical

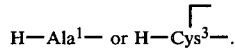

The meaning of the symbol X′ corresponds fairly extensively to that of the α-amino-protecting groups that are used in the synthesis of the peptide chain and described in detail hereinbelow. Preferably, similar or, more preferably, identical, protecting groups are used both in the radical $A_o$ and in the radical $Ac_o$ and are split off simultaneously following the acylation reaction.

A reactive derivative of an acid $Ac_oOH$ is, for example, an anhydride, especially a symmetric anhydride of the formula $Ac_o$—O—$Ac_o$ or a cyclic anhydride of a dicarboxylic acid, such as succinyl anhydride or glutaryl anhydride, or alternatively a mixed anhydride with a different organic acid, for example with trifluoroacetic acid, or especially with an inorganic acid, for example an acid azide or acid halide, especially an acid chloride. A reactive acid derivative is preferably an activated ester, for example one in which the acid Ac$_o$OH is esterified with 2,4,5-trichlorophenol, pentachlorophenol, pentafluorophenol, 2-nitrophenol or especially 4-nitrophenol, or with an N-hydroxy compound, such as N-hydroxysuccinimide, 1-hydroxybenzotriazole or N-hydroxypiperidine, or alternatively with an N,N'-disubstituted isourea, such as especially N,N'-dicyclohexylisourea, or a similar activating component known from peptide chemistry, cf. Houben-Weyl: Methoden der organischen Chemie; 4th edition, vol. 15/I and II, E. Wünsch (editor): Synthese von Peptiden (Georg Thieme Verlag, Stuttgart; 1974).

The acylation is effected in a manner known per se, preferably in customary solvents, for example dioxan, tetrahydrofuran, acetonitrile, pyridine, dimethylformamide, dimethylacetamide, dimethyl sulphoxide, N-methylpyrrolidone, hexamethylphosphoric acid triamide, chloroform and methylene chloride, and in advantageous mixtures thereof. Alternatively, an organic base, for example a quaternary or especially a tertiary amine, such as triethylamine, N-ethylmorpholine or N-methylpiperidine, can be added to obtain the amino group which is to be acylated in deprotonated form. The reaction temperature is usually from $-20°$ to $+70°$ C., preferably from approximately 0° C. to room temperature.

Active esters are generally advantageous as acylating agents because they preferentially acylate amino groups before hydroxyl groups and thus render protection of hydroxyl groups virtually superfluous. In the case of dicarboxylic acids, however, cyclic anhydrides are preferred, if they are available. In order to avoid undesired O-acylation, only one equivalent of the acylating agent is usually used for each free amino group of the starting material of the formula II.

If, however, it is more advantageous for some reason to dispense with selective acylation, as may be the case especially in the reaction with acid chlorides, the acylating agent is used in excess and the co-acylated hydroxyl groups are liberated subsequently in the same conventional manner as the protected hydroxyl groups, especially by basic hydrolysis, for example with sodium or potassium hydroxide in the presence of water.

The subsequent splitting off of any protecting groups present depends on their type and is carried out in each case in a conventional manner known per se, as described in detail hereinbelow. The splitting off of any hydroxyl-protecting groups Y and α-amino-protecting groups X' present in the radicals A$_o$ and Ac$_o$ is an obligatory measure; on the other hand, an ε-amino-protecting group X in the lysine residue in the 4-position is split off only if desired.

The acylpeptides according to the invention can also be manufactured by cyclising a linear peptide corresponding to the acylpeptide, optionally while temporarily protecting any free hydroxyl, carboxyl and/or amino groups. A corresponding linear peptide is one which has the same amino acids in a sequence identical to that of the cyclic peptides according to the invention, a bond between any two adjacent ring-forming amino acids being, however, interrupted and replaced by corresponding terminal functional groups which may be present also in an activated form. If the ring is interrupted at the amide bond between any two successive amino acids, the terminal groups of the linear peptide are a carboxyl group and an amino group; if, however, the ring is interrupted between two cysteine residues, such as especially between those in the 3- and 14-positions, then a disulphide bond is broken, and the corresponding linear peptide has as terminal groups two free or functionally modified mercapto groups. Depending on the specific type of terminal groups, appropriate cyclisation processes are used.

The compounds according to the invention can thus be manufactured by cyclisation by cyclising a corresponding linear peptide of the formula $$H\text{—}[I_a]\text{—}V \qquad (III),$$

in which $I_a$ represents a radical corresponding to the formula I in which the amide bond between any two adjacent amino acid residues of the peptide ring is interrupted, and V represents a free hydroxyl group, a hydroxyl group modified by an activating group or represents the hydrazino group —NH—NH$_2$, any amino, carboxyl and hydroxyl groups present that do not participate in the cyclisation reaction being, as required, in protected form and liberated subsequently.

Of the linear peptides of the formula III, those in which the radical A is present as a terminal amino acid in the radical [Ia] are preferred. These preferred starting materials are characterised by the formulae

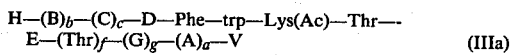

and especially

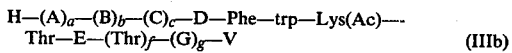

in which Ac, A, B, C, D, trp, E and G, and also a, b, c, f and g have the meanings given at the beginning and V has the meanings given immediately above. Most especially preferred are compounds of the formulae IIIa and IIIb in which there are no sulphur-containing amino acids in the radical A.

A functional group represented by the symbol V supplements the carbonyl group of the C-terminal amino acid residue and forms together with that group a free carboxyl group, an activated ester group or the carbazolyl group, as the case may be.

The activating group by which the hydroxyl group is modified is especially one that forms the activated ester of N-hydroxysuccinimide, 1-hydroxybenzotriazole, N,N'-dicyclohexylisourea, 2,4,5-trichlorophenol, 2-nitrophenol, 4-nitrophenol, pentachlorophenol or pentafluorophenol but may also be a different activating group of this type known from peptide chemistry, cf. Houben-Weyl, volume 15/II.

The cyclisation according to the invention of the linear peptides of the formula III is carried out in a manner known per se by means of conventional coupling methods customarily used for the formation of the amide bond, the peptide starting materials, however, being used in a very low concentration in order to influence the course of the coupling operation in favour of intramolecular cyclisation at the expense of intermolecular polycondensation.

The linear peptides are advantageously used in an approximately $1.10^{-4}$ molar to approximately $1.10^{-2}$ molar concentration, preferably an approximately $1.10^{-3}$ molar concentration, which corresponds to a weight/volume concentration of approximately 0.01 to 1.0%, preferably 0.1%. The reaction mixture can be correspondingly diluted from the start or this dilution can be produced continuously by the slow dropwise addition of the starting material, and optionally the other reagents, to the reaction mixture.

Cyclisation is preferably carried out, at a starting concentration indicated above, by (a) treating a starting material of the formula III, in which V represents a free hydroxyl group, while temporarily protecting other amino, carboxyl and hydroxyl groups, with a carbodiimide, optionally in the presence of an active ester-forming component, or (b) reacting with an organic base a starting material of the formula III, in which V represents a hydroxyl group modified to form the activated ester and the terminal amino group is present in protonated form, at least the amino groups and carboxyl groups not participating in the cyclisation reaction being protected, or (c) first treating a starting material of the formula III, in which V represents the group —NHNH$_2$ and at least the amino groups not participating in the cyclisation reaction are protected, with nitrous acid or a lower alkyl ester thereof under acidic conditions and then cyclising with excess organic base at an above-mentioned low concentration.

A carboxyl group is protected by a protecting group W in the manner described hereinbelow. For the protection of the amino and hydroxyl groups, the groups X and X', and Y respectively, are advantageously used.

The cyclisation is carried out in suitable solvents, for example dioxan, tetrahydrofuran, acetonitrile, pyridine, dimethylformamide, dimethylacetamide, dimethyl sulphoxide, N-methylpyrrolidone, hexamethylphosphoric acid triamide, chloroform, methylene chloride or ethyl acetate, and mixtures thereof.

In process variant (a) the cyclisation is brought about by a carbodiimide, preferably N,N'-dicyclohexyl carbodiimide, which is advantageously used in excess; it is to be assumed that the starting material of the formula III having a free carboxyl group is first converted into an activated ester of dicyclohexylisourea (or an analogous isourea) and this active ester formed in situ immediately reacts further. The intermediate formation of an active ester can doubtless be attributed to the addition of an active ester-forming component as an auxiliary reagent; for this purpose, active ester-forming components customary in peptide chemistry may be used, such as, especially, 2,4,5-trichlorophenol, 2- or 4-nitrophenol, pentachlorophenol and pentafluorophenol, but, more especially, N-hydroxy compounds, among which N-hydroxysuccinimide, N-hydroxypiperidine and above all 1-hydroxybenzotriazole are especially advantageous. In the case of this variant, the operating temperature is generally 0°–70°, preferably 35°–55°.

In the case of variant (b) which is carried out with ready-prepared active esters, especially those already pointed out, cyclisation takes place spontaneously as soon as the terminal amino group is deprotonated by the organic base. The bases used are preferably quaternary or especially tertiary amines, for example triethylamine or N-ethylmorpholine. The operation is preferably carried out at 10°–30°, especially at room temperature.

In the case of variant (c), the first phase, i.e. the formation of the acid azide by treating with nitrous acid or an ester thereof, may advantageously be carried out at a considerably higher concentration of the starting materials than in the case of the subsequent cyclisation. The operation is advantageously carried out with approximately one equivalent of a lower alkyl nitrite, such as ethyl nitrite, isoamyl nitrite and especially tert.-butyl nitrite, in a hydrochloric acid medium at temperatures of from approximately −30° to approximately −5°, preferably approximately −20°; a slight excess of nitrite is permissible. The solution of the azide formed is then, after the necessary dilution, rendered basic at a temperature of from approximately 0° to approximately 35° by means of excess organic base, for example one of those mentioned above, and thereby made to cyclise spontaneously as in the case of process variant (b).

In special cases, the compounds according to the invention, if they contain a pair of sulphur-containing amino acid residues, such as those of D- or L-cysteine or β-mercaptopropionic acid, can be manufactured by oxidising a corresponding linear peptide of the formula $$T_o\text{—}[I_s]\text{—}T_o \qquad (IV),$$

in which $I_s$ represents a radical corresponding to the formula I in which the disulphide bond between the sulphur-containing amino acid residues is interrupted, and $T_o$ represents hydrogen or a mercapto-protecting group T, to form the disulphide bridge, optionally having split off the mercapto-protecting groups T beforehand or splitting them off at the same time, and by liberating amino, carboxyl and/or hydroxyl groups present optionally in protected form.

The linear peptide IV is especially one of the formula

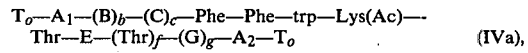

in which
A$_1$ represents

$T_o$ has the meaning given immediately above and the other symbols have the meanings given at the beginning.

The linear peptide IV is, however, alternatively one of the formula

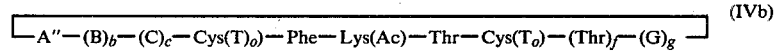

(IVb)

in which A" denotes a sulphur-free amino acid residue mentioned under the meanings of A, $T_o$ has the meaning given immediately above and the other symbols have the meanings given at the beginning.

Cyclisation by oxidation is carried out in the conventional manner generally known per se. It is possible to oxidise a linear peptide of the formula IV in which all the protecting groups have previously been split off. If, however, the linear peptide of the formula IV is in a form having protected amino, hydroxyl and/or carboxyl groups, as is obtained in most instances in the case of prior synthesis, it is advantageous to carry out the cyclisation first and only then to split off the protecting groups (i.e. the groups X, X', Y and W). In that case, preferably any carboxyl groups present are protected as tert.-butyl esters, $\epsilon$-amino groups are protected by the tert.-butoxycarbonyl group, the hydroxyl groups of the serine and threonine residues are protected, if at all, as tert.-butyl ethers, and the mercapto groups are protected by trityl, acetaminomethyl, p-methoxybenzyl, PCH or MPCH, or by tetrahydropyranyl groups (Thp). Apart from acetaminomethyl, all these functional groups can be split off in one step by the action of acids (acidolysis). Mercapto-protecting groups of the trityl, acetaminomethyl or tetrahydropyranyl type may, however, if desired, be split off selectively with heavy metal salts, for example mercuric acetate, and hydrogen sulphide, while protecting groups of the tert.-butyl type are retained. In this manner, there is obtained a linear peptide having free mercapto groups which can be cyclised by oxidation in a manner known per se, for example with iodine, with diiodoethane in organic solvents, or with oxygen, especially atmospheric oxygen, such as with atmospheric oxygen in liquid ammonia. It is even more advantageous to remove the trityl, tetrahydropyranyl or acylaminomethyl groups protecting the mercapto groups while simultaneously forming the disulphide bridge with iodine, for example in methanol, acetic acid or especially dimethylformamide, the other protecting groups of the type mentioned being retained and split off subsequently.

The narrower choice of protecting groups is determined by the specific purpose, it being necessary especially in the case where several functional groups are to be protected to select advantageous combinations.

As $\epsilon$-amino-protecting groups X it is possible to use any of the amino-protecting groups that are customary in peptide chemistry, as are described synoptically in the appropriate reference works, for example in Houben-Weyl: Methoden der oganischen Chemie; 4th edition, vol. 15/I, E. Wünsch (editor): Synthese von Peptiden; (Georg Thieme Verlag, Stuttgart; 1974).

Thus, for example, amino-protecting groups that can be split off by reduction or by bases can be used, for example especially the benzyloxycarbonyl group and benzyloxycarbonyl groups that are substituted in the aromatic moiety by halogen atoms, nitro groups, lower alkoxy groups and/or lower alkyl radicals, such as p-chloro- and p-bromobenzyloxycarbonyl, p-nitrobenzyloxycarbonyl, p-methoxybenzyloxycarbonyl or p-tolyloxycarbonyl groups, or alternatively by the isonicotinyloxycarbonyl group, and also by acyl groups, such as p-toluenesulphonyl, benzenesulphenyl, o-nitrobenzenesulphenyl groups or formyl, trifluoroacetyl or phthaloyl.

An advantageous $\epsilon$-amino-protecting group X is an ethoxycarbonyl group which carries, in the $\beta$-position, a silyl group substituted by three hydrocarbon radicals, such as triphenylsilyl, dimethylbutyl-silyl or especially a trimethylsilyl group. A $\beta$-(trihydrocarbylsilyl)-ethoxycarbonyl group of this type, such as a $\beta$-(tri-lower alkylsilyl)-ethoxycarbonyl group, for example especially the $\beta$-(trimethylsilyl)-ethoxycarbonyl group, forms, together with the $\epsilon$-amino group that is to be protected, a corresponding $\beta$-trihydrocarbylsilylethoxycarbonylamino group (for example, the $\beta$-trimethylsilylethoxycarbonylamino group), which is stable under the conditions of acid hydrolysis and hydrogenolysis, but can be split off by the action of fluoride ions under quite specific, very mild conditions. In this respect, it behaves analogously to the $\beta$-silylethyl ester group described hereinbelow as a carboxyl-protecting group. (This similarity must be given particular consideration during the synthesis: but for isolated cases, the use of one of these protecting groups excludes the simultaneous use of the other protecting group.) Further details are given below in connection with the protection of the carboxyl group as $\beta$-silylethyl ester.

Groups that can be split off by acidolysis are most especially preferred, such as especially the tert.-butoxycarbonyl group and analogous groups, for example the tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl groups, and groups of the aralkyl type, such as benzhydryl and triphenylmethyl (trityl), or certain aralkoxycarbonyl groups of the 2-(p-biphenylyl)-2-propoxycarbonyl type, which are described in Swiss Patent Specification No. 509 266.

As the hydroxyl-protecting group Y there can be used any of the groups customarily used for this purpose in peptide chemistry, cf. the work cited above (Houben-Weyl). Groups that can be split off by acidolysis, such as 2-tetrahydropyranyl and more especially tert.-butyl, or tert.-butoxycarbonyl, are preferred. Alternatively, however, hydroxyl-protecting groups that can be split off by reduction or by means of bases can be used, for example benzyl and benzyloxycarbonyl groups that may be substituted in the aromatic moiety by halogen, nitro and/or lower alkoxy, or lower alkanoyl radicals, such as acetyl, or aroyl radicals, such as benzoyl. It is also possible to proceed without protecting hydroxyl groups if certain limiting measures are observed.

As carboxyl-protecting groups W there can be used any group customarily used for this purpose, cf. the work cited above (Houben-Weyl). Thus, carboxyl groups are protected, for example, by the formation of hydrazides or by esterification. Suitable for esterification are, for example, lower optionally substituted alkanols, such as methanol, ethanol, cyanomethyl alcohol, 2,2,2-trichloroethanol, benzoylmethyl alcohol or especially tert.-butyl alcohol, or alternatively an optionally substituted benzyl alcohol. An especially advantageous category of substituted alkanols is ethyl alcohols that contain in the $\beta$-position a tri-substituted silyl group, such as a triphenylsilyl, a dimethyl-butylsilyl or especially a trimethylsilyl group. As described, for example, in Belgian Patent Specification No. 851,576, these alcohols are especially suitable for protecting carboxyl groups because, although the corresponding $\beta$-silylethyl esters, for example $\beta$-(trimethylsilyl)-ethyl ester, have the stability of conventional alkyl esters, they can be split off selectively under mild conditions by the action of fluoride ions while all the other protecting groups are retained.

As a mercapto-protecting group T there can be used any of the groups customarily used for this purpose in peptide chemistry, the mercapto groups being protected especially by suitable acylation or alkylation. Suitable for acylation is, for example, the acetyl or benzoyl radical, a lower alkylcarbamoyl group, (for example ethylcarbamoyl), or a benzyloxycarbonyl group optionally substituted, for example, as stated above. Suitable for alkylation are, for example, tert.-butyl, isobutoxymethyl, benzylthiomethyl or tetrahydropyranyl radicals or arylmethyl radicals optionally substituted by halogen, lower alkoxy or nitro, such as benzyl, p-methoxybenzyl, diphenylmethyl, dimethoxybenzhydryl or more especially trityl, and also phenylcyclohexyl (PCH), p-methoxyphenylcyclohexyl (MPCH), thien-2-ylcyclohexyl, et.al., cf. Ber. 101, 681 (1968). An acylaminomethyl radical of the general formula $R_f$—CO—NH—CH$_2$—, in which $R_f$—CO— denotes the radical of a carboxylic acid is also very advantageous, cf. Tetrahedron Letters 1968 (26), 3057 and German Offenlegungsschrift No. 2 060 969. The acyl radical $R_f$—CO— can be derived from an aliphatic, cycloaliphatic, aromatic, araliphatic or heterocyclic carboxylic acid or a carbonic acid mono-derivative (such as a carbonic acid monoester or a carbamic acid). The symbol $R_f$ represents especially an optionally substituted lower alkyl radical, for example a methyl, ethyl, propyl, isopropyl, n-butyl or tert.-butyl radical, which may contain as substituents, for example chlorine, trifluoromethyl or the nitro group. $R_f$ also represents, for example, an optionally substituted cycloalkyl radical having 3–8, preferably 5 or 6, ring atoms, such as the cyclopentyl or cyclohexyl radical, or an optionally substituted aromatic or araliphatic, preferably monocyclic, radical, especially an optionally substituted phenyl or benzyl radical, for example unsubstituted phenyl or benzyl, or phenyl or benzyl substituted in the phenyl moiety by lower alkyl, lower alkoxy, halogen or nitro, or a monocyclic heterocyclyl radical, for example thienyl or furyl. Of the acylaminomethyl groups, the acetylaminomethyl group is especially preferred.

The protecting groups Y and W, and also the α-amino-protecting group X' characterised in more detail below, are preferably so chosen that they can be split off under similar conditions; especially preferred in this connection are the groups already pointed out above that can be split off by acidolysis. All these protecting groups can thus be split off advantageously in a single operation; it is also possible, however, to use different kinds of protecting group and to split off each one individually.

If, however, a protecting group X, i.e. an ε-amino-protecting group present in the Lys$^4$ residue, is to be retained in the end product of the formula I, the radicals X', Y and W should be so chosen that they can be split off while group X is retained.

The protecting groups are split off in the generally known manner; acid hydrolysis (acidolysis) is carried out, for example, by means of trifluoroacetic acid, hydrochloric acid or hydrofluoric acid, or, in the case of protecting groups that are sensitive to acids, by means of a lower aliphatic carboxylic acid, such as formic acid and/or acetic acid, in the presence of water and optionally a poly-halogenated lower alkanol or lower alkanone, such as 1,1,1,3,3,3-hexafluoropropan-2-ol or hexafluoroacetone. The groups that can be split off by reduction, especially those which contain benzyl radicals, are preferably removed by hydrogenolysis, for example by hydrogenation under palladium catalysis. The isonicotinyloxycarbonyl group is split off preferably by zinc reduction.

Those end products according to the invention which contain basic groups are obtained as bases or as acid addition salts depending on the method of isolation; these can subsequently be inter-converted in a manner known per se. Similarly, end products having acidic groups may also be in the form of salts, it being possible to convert each form into the other in known manner.

The formation of the above-mentioned complexes also is carried out according to known methods; complexes with sparingly soluble metal compounds, for example aluminium or zinc compounds, are produced preferably in a manner analogous to that known for ACTH, for example by reaction with a soluble salt of the metal concerned, for example zinc chloride or zinc sulphate, and precipitation with an alkali metal phosphate and/or hydroxide. Complexes with organic compounds of the type polyoxygelatine, carboxymethylcellulose, polyvinylpyrrolidone, polyphloretin phosphate, polyglutamic acid, etc. are obtained by mixing these substances with the peptide in aqueous solution. In the same manner, insoluble compounds may also be manufactured with alkali metal polyphosphates.

The starting materials of the above-characterised formulae III and IV and, unless stated otherwise, the intermediates used for the synthesis thereof, are new and, in some cases, can be used advantageously also for the synthesis of other somatostatin analogues, for example those having analogous amino acid partial sequences. The present invention relates to these starting materials and the processes for the manufacture thereof. They are obtained by methods known per se, by condensing with one another, in any time sequence, the amino acids and smaller peptide units necessary for their synthesis with the formation of CO—NH bonds, it being possible to protect temporarily any functional groups not participating in the reaction.

In the manufacture of these starting materials, and also of all the necessary intermediates, suitable protecting groups for the terminal α-amino and carboxyl groups are especially the protecting groups that are customarily used in the synthesis of long-chain peptides and that can be split off readily and selectively, for example by solvolysis or reduction. They have already been mentioned above several times under the symbols X' and W, respectively.

Examples of α-amino-protecting groups X' are: di- or triaryl-lower alkyl groups optionally substituted, for example, by halogen, nitro, lower alkyl or lower alkoxy, such as diphenylmethyl or triphenylmethyl groups, for example benzhydryl, trityl, di-(p-methoxy)-benzhydryl, or especially groups derived from carbonic acid that can be split off by hydrogenolysis, such as benzyloxycarbonyl groups optionally substituted in the aromatic moiety by halogen atoms, nitro groups, lower alkyl or lower alkoxy groups, for example benzyloxycarbonyl, p-bromo- or p-chlorobenzyloxycarbonyl, p-nitrobenzyloxycarbonyl, p-methoxybenzyloxycarbonyl; also 2-(p-biphenylyl)-2-propoxycarbonyl and similar aryloxycarbonyl groups described in Swiss Patent Specification No. 509 266. It must be ensured that the α-amino-protecting group X' can be split off selectively while the optionally present ε-amino-protecting group X of the lysine residue in the 4-position is retained. Furthermore, it is often advantageous if, during the splitting off of the α-amino-protecting group, an optionally present carboxyl- or hydroxyl-protecting group W or Y also remains undamaged.

The carboxyl-protecting groups for this purpose are the same as those discussed above in connection with the corresponding meaning of the symbol W.

These protecting groups can be split off in known manner. Thus, the benzyloxycarbonyl group can be split off by hydrogenolysis, the N-trityl group by mineral acids, such as hydrohalic acids, for example hydrofluoric acid or preferably hydrochloric acid, or an organic acid, such as formic acid, acetic acid, chloroacetic acid or trifluoroacetic acid, in aqueous or absolute trifluoroethanol as the solvent (cf. German Offenlegungsschrift DT No. 2 346 147) or with aqueous acetic acid; the tert.-butoxycarbonyl group can be split off with trifluoroacetic acid or hydrochloric acid, the 2-(p-biphenylyl)-isopropoxycarbonyl group with aqueous acetic acid or, for example, a mixture of glacial acetic acid, formic acid (82.8% strength) and water (7:1:2) or in accordance with the process described in DT-OS No. 2 346 147.

The β-silylethyl ester groups are split off preferably with reagents that yield fluoride ions, for example fluorides of quaternary organic bases, such as tetraethylammonium fluoride. Alternatively, however, they may be split off, in the same manner as conventional alkyl esters, by alkaline hydrolysis, for example by means of alkali metal hydroxides, carbonates or bicarbonates, or may be converted into the corresponding carbazoyl groups by hydrazinolysis, for example by means of hydrazine hydrate. Acidolysis is preferably used for splitting off tert.-butyl esters and hydrogenolysis for benzyl esters.

The condensation of the amino acids and/or peptide units which must be effected for the manufacture of the starting materials of the formula III or IV is carried out in a manner known per se, preferably by linking an amino acid or a peptide having a protected α-amino group and an optionally activated terminal carboxyl group (=active component) to an amino acid or a peptide having a free α-amino group and a free or protected, for example esterified, terminal carboxyl group (=passive component), liberating the terminal amino group in the product so formed and reacting this peptide, which contains a free α-amino group and an optionally protected terminal carboxyl group, with a further active component, i.e. an amino acid or a peptide having an activated carboxyl group and a protected α-amino group, and so on. The carboxyl group can be activated, for example, by converting it into an acid azide, anhydride, imidazolide, isoxazolide or an activated ester, such as one of those mentioned hereinbelow, or by reacting it with a carbodiimide, such as N,N'-dicyclohexyl carbodiimide, optionally with the addition of N-hydroxysuccinimide or an unsubstituted or, for example, a halogen-, methyl- or methoxy-substituted 1-hydroxybenzotriazole or 4-hydroxybenzo-1,2,3-triazine-3-oxide (inter alia cf. DT No. 1 917 690, DT No. 1 937 656, DT No. 2 202 613), or especially N-hydroxy-5-norbornene-2,3-dicarboximide, or with N,N'-carbonyldiimidazole. The most usual coupling method is the carbodiimide method, also the azide method, the activated esters method and the anhydride method, the Merrifield method and the method using N-carboxyanhydrides or N-thiocarboxyanhydrides.

Suitable for the formation of activated esters, such as those mentioned above, are, for example, phenols and thiophenols optionally substituted by electron-attracting substituents, such as phenol, thiophenol, thiocresol, p-nitrothiophenol, 2,4,5- and 2,4,6-trichlorophenol, pentachlorophenol, o- and p-nitrophenol, 2,4-dinitrophenol, and p-cyanophenol, and also, for example, N-hydroxysuccinimide, N-hydroxyphthalimide and N-hydroxypiperidine.

In an especially preferred method of manufacture of the peptides of the formulae III and IV, the coupling method used is the carbodiimide method with N,N'-dicyclohexyl carbodiimide in the presence of 1-hydroxybenzotriazole. The terminal carboxyl group is protected in the form of the β-(trimethylsilyl)-ethyl ester, and the α-amino group of the active component is protected by the benzyloxycarbonyl group which is split off by hydrogenolysis after each coupling step. In order to protect the ε-amino group of the lysine residue in the 4-position, acylation with the tert.-butoxycarbonyl group is used and, for the hydroxyl group of the serine and threonine residues, etherification with the tert.-butyl group. These two protecting groups may, if desired, be split off finally in one step by acid hydrolysis, for example by means of trifluoroacetic acid, hydrochloric acid or hydrofluoric acid. The ε-amino group of the lysine residue in the 9-position is present in acylated form and therefore requires no protection.

The sulphur-containing amino acid residues (Bmp and cys) are introduced preferably only in the last stages of the synthesis since, as is known, the presence of sulphur can impair the activity of the hydrogenation catalysts and hence plate in doubt the use of the otherwise very advantageous groups that can be split off by hydrogenolysis. The mercapto groups in the said acids are advantageously protected by the trityl groups which are especially suitable for carrying out preferred variants of the process.

Depending on the procedure used, the compounds of the formulae III and IV are obtained, depending on their character, in the form of bases or acid addition salts or, alternatively, in the form of acids or their salts. The bases can be obtained from the acid addition salts in a manner known per se. Therapeutically acceptable acid addition salts can, in their turn, be obtained from the bases by reacting with acids, for example with those that form the above-mentioned salts. Acids and their salts stand in a similar relationship to each other. Compounds that have both a free carboxyl group and a basic group may be in the form of internal salts.

Owing to the close relationship between the new compounds in free form and in the form of their salts, hereinbefore and hereinafter the term "free compounds" shall, if desired, also include the salts thereof and the term "salts" shall, if desired, also include the free compounds, here appropriate according to meaning and purpose.

The invention relates also to those embodiments of the process in which a compound obtained as an intermediate at any stage of the process is used as starting material and the remaining process steps are carried out, or in which a starting material is formed under the reaction conditions or is used in the form of a derivative, for example a salt.

In the process of the present invention, the starting materials used are preferably those that result in the compounds described at the beginning as especially valuable.

The present invention relates also to pharmaceutical preparations that contain compounds of the formula I or pharmaceutically acceptable salts or complexes thereof. These preparations may be used especially in the abovementioned indications if they are administered intraperitoneally, such as intravenously, intramuscularly or subcutaneously, or also intranasally. The necessary dose depends on the particular disorder to be treated, its severity and the duration of therapy. The number and quantity of the individual doses and also the administration scheme can best be determined on the basis of an individual examination of the patient concerned. The method of determining these factors is known to the man skilled in the art. As a rule, however, in the case of injection, a therapeutically active quantity of a compound of this type lies in the dosage range of approximately 0.001 to approximately 0.2 mg/kg body weight. Preferably, the range is approximately 0.0015 to approximately 0.15 mg/kg body weight and administration is by intravenous infusion or subcutaneous injection. Accordingly, pharmaceutical preparations for parenteral administration in unit dose form contain per dose, depending on the type of medication, approximately 0.08 to approximately 15 mg of one of the compounds according to the invention. Apart from the active substance, they usually also contain a buffer, for example a phosphate buffer, that is to maintain the pH between approximately 3.5 and 7, and also sodium chloride, mannitol or sorbitol for adjusting the isotonicity. They may be in freeze-dried or dissolved form and solutions may advantageously contain an antibacterially active preservative, for example 0.2–0.3% of 4-hydroxybenzoic acid methyl ester or ethyl ester. If the active substance in such preparations is to be in the form of a complex having a prolonged duration of action then it may be formed directly by adding the complex-forming components to an injection solution that is prepared, for example, according to the above-mentioned methods. A suitable additive is, for example, 0.1–1.0% by weight of a zinc(II) salt (for example sulphate) in conjunction with 0.5–5.0% by weight of protamine (for example as a sulphate), calculated on the total volume of the injection solution; this preparation is in the form of a solution having a pH of 3.5 to approximately 6.5 or in the form of a suspension having a pH of approximately 7.5 to 8.0.

A preparation for intranasal administration may be an aqueous solution or gel, an oily solution or suspension, or alternatively a fat-containing salve. A preparation in the form of an aqueous solution is obtained, for example, by dissolving the active substance of the formula I, or a therapeutically acceptable acid addition salt thereof, in an aqueous buffer solution having a pH of up to 7.2 and adding a substance producing isotonicity. A polymeric adhesive, for example polyvinylpyrrolidone, and/or a preservative are advantageously added to the aqueous solution. The individual dose is approximately 0.08 to approximately 15 mg, preferably 0.25 to 10 mg, which are contained in approximately 0.05 ml of a solution or 0.05 g of a gel.

An oily form of medication for intranasal administration is obtained, for example, by suspending a peptide of the formula I, or a therapeutically acceptable acid addition salt thereof, in an oil, optionally with the addition of swelling agents, such as aluminium stearate, and/or interfacially active agents (surfactants), the HLB value ("hydrophilic-lipophilic balance") of which is less than 10, such as fatty acid monoesters of polyhydric alcohols, for example glycerine monostearate, sorbitan monolaurate, sorbitan monostearate or sorbitan monoleate. A fat-containing salve is obtained, for example, by suspending the active substance according to the invention in a spreadable fat base, optionally with the addition of a surfactant having a HLB value of less than 10. An emulsion salve is obtained by triturating an aqueous solution of the peptide active substance in a soft, spreadable fat base with the addition of a surfactant the HLB value of which is less than 10. All these intranasal forms of medication may also contain preservatives. The individual doses are approximately 0.08 to approximately 15 mg, preferably 0.25 to 10 mg, contained in approximately 0.05 to approximately 0.1 g of the base substance.

Also suitable for intranasal administration are inhalation or insufflation preparations, such as insufflation capsules that permit the active substance to be insufflated in the form of a powder with respiratory air, or aerosols or sprays that can disperse the pharmacological active substance in the form of a powder or in the form of drops of a solution or suspension. Preparations having powder-dispersing properties generally contain adjuncts in addition to the active substance: insufflation capsules contain, for example, solid carriers, such as lactose; aerosol or spray preparations contain, for example, a liquid propellant having a boiling point of below room temperature and, if desired, other carriers, such as liquid or solid non-ionic or anionic surfactants and/or solid diluents. Preparations in which the pharmacological active substance is in solution contain, in addition to this, a suitable propellant and also, if necessary, an additional solvent and/or a stabiliser. Instead of the propellant, it is also possible to use compressed air which is produced when required by means of a suitable compressing and releasing device.

The invention relates also to the use of the novel compounds of the formula I and therapeutically acceptable acid addition salts thereof as pharmacologically active compounds, especially in the indications mentioned at the beginning, preferably in the form of pharmaceutical preparations. The daily dose administered to a warm-blooded animal weighing approximately 70 kg is from approximately 0.1 to approximately 120 mg.

The invention is illustrated in the following Examples but is not limited by these. Temperatures are given in degrees Centigrade; the conventional short forms, for example those compiled in "Synthese von Peptiden" (editor: E. Wünsch), volume XV of "Methoden der org. Chemie" (Houben-Weyl) (1974; G. Thieme, Stuttgart) are used as abbreviations, for example for denoting amino acids, peptides, protecting groups, etc. The following abbreviations, in particular, are used:

| Boc | tert.-butoxycarbonyl |
|---|---|
| But | tert.-butyl (as ether-forming group) |
| OTmse | 2-(trimethylsilyl)-ethoxy (as ester-forming group) |
| Z | benzyloxycarbonyl |
| TLC | thin layer chromatography. |

In TLC, unless otherwise indicated, silica gel is used as the adsorbent and the following systems are used as eluants:

| System | |
|---|---|
| 52: | n-butanol/acetic acid/water (71.5:7.5:21) |
| 101: | n-butanol/pyridine/acetic acid/water (38:24:8:30) |
| 104: | chloroform/methanol/17% aqueous ammonia (41:41:18) |
| 111B: | n-butanol/pyridine/25% aqueous ammonia/water (40:24:6:30) |
| 112A: | n-butanol/pyridine/formic acid/water (42:24:4:20) |
| 151: | n-butanol/pyridine/acetic acid/water (38:20:6:24) |
| 157: | chloroform/methanol/water/acetic acid (70:42:10:0.5) |
| 157B: | chloroform/methanol/water/acetic acid |

-continued

| | |
|---|---|
| | (85:13:1.5:0.5) |
| 157C: | chloroform/methanol/water/acetic acid (75:27:5:0.5) |
| 157E: | chloroform/methanol/water/acetic acid (55:47:13:5) |

EXAMPLE 1

[$N^\alpha$—acetyl-Ala$^1$, $N^\epsilon$—acetyl-Lys$^4$, $N^\epsilon$—acetyl-Lys$^9$]somatostatin

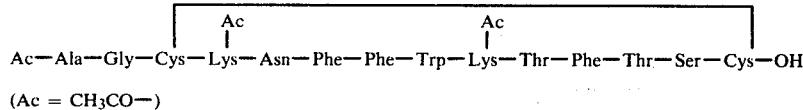

(Ac = CH$_3$CO—)

50 mg of somatostatin (peptide content 82%, remainder water and acetic acid) in 175 μl of dimethylformamide are stirred with 16 mg of 4-nitrophenyl acetate and 12 μl of triethylamine for 2 hours at room temperature. The product, precipitated with ether/hexane, is filtered in chloroform/methanol (1:1) over a Sephadex LH-20 ® column and the fractions that are pure according to TLC are isolated. Yield: 44 mg.

TLC: [chloroform/methanol/water/glacial acetic acid (55:47:13:0.5)]
$R_f$: 0.46.

EXAMPLE 2

[D-Trp$^8$, $N^\epsilon$—acetyl-Lys$^9$—Gaba$^{12}$]cyclosomatostatin(5–12)octapeptide

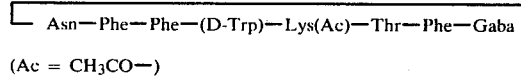

(Ac = CH$_3$CO—)

100 mg of

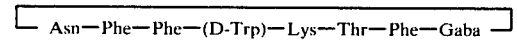

(in the form of the acetate) together with 15 μl of N-methylmorpholine and 20 mg of p-nitrophenyl acetate are dissolved in 1.0 ml of dimethylformamide and kept at room temperature for 20 hours. For working up, the reaction mixture is taken up in 20 ml of ethyl acetate and washed 3 times using 5 ml of water each time. After drying over sodium sulphate, the organic phase is concentrated by evaporation in vacuo. The residue is triturated with 5 ml of ether, filtered off and washed with ether. The crude product is chromatographed on a silica gel column (70 g) by means of a chloroform/methanol mixture (with the proportion of methanol gradually increasing from 5 to 15%). Suitable fractions that are uniform according to thin-layer chromatography are combined, concentrated by evaporation in vacuo, dissolved in 20 ml of tert.-butanol and lyophilised.

| TLC: | [CHCl$_3$/CH$_3$OH/H$_2$O (14:6:1)] | $R_f$: 0.65 |
|---|---|---|
| | [CHCl$_3$/CH$_3$OH (85:15)] | $R_f$: 0.20 |
| | [n-butanol/acetic acid/H$_2$O (3:1:1)] | $R_f$: 0.77 |

The following $N^\epsilon$-acyl-Lys$^9$ derivatives are obtained from the same peptide (in the form of the free base) in an analogous manner while observing the other conditions, and serve as intermermediates for the end products of the following Example 3:

(a) The $N^\epsilon$-(N-benzyloxycarbonylglycyl)-Lys$^9$ derivative (Ac=Z-Gly) is obtained with 33 mg of Z-Gly-p-nitrophenyl ester

| TLC: | [CHCl$_3$/CH$_3$OH/H$_2$O (14:6:1)] | $R_f$: 0.74 |
|---|---|---|
| | [CHCl$_3$/CH$_3$OH (85:15)] | $R_f$: 0.29 |

(b) The $N^\epsilon$-(N-benzyloxycarbonylleucyl)-Lys$^9$ derivative (Ac=Z-Leu) is obtained with 38 mg of Z-Leu-p-nitrophenyl ester

| TLC: | [CHCl$_3$/CH$_3$OH/H$_2$O (14:6:1)] | $R_f$: 0.80 |
|---|---|---|
| | [CHCl$_3$/CH$_3$OH (85:15)] | $R_f$: 0.35 |

(c) The $N^\epsilon$-(N-benzyloxycarbonylphenylalanyl)-Lys$^9$ derivative (Ac=Z-Phe) is obtained with 42 mg of Z-Phe-p-nitrophenyl ester.

| TLC: | [CHCl$_3$/CH$_3$OH/H$_2$O (14:6:1)] | $R_f$: 0.84 |
|---|---|---|
| | [CHCl$_3$/CH$_3$OH (85:15)] | $R_f$: 0.39 |

(d) The $N^\epsilon$-(N-benzyloxycarbonylprolyl)-Lys$^9$ derivative (Ac=Z-Pro) is obtained with 39 mg of Z-Pro-p-nitrophenyl ester.

| TLC: | System 157B | $R_f$: 0.35 |
|---|---|---|

(e) The $N^\epsilon$-($N^\alpha$-tert.-butoxycarbonyl-$N^\epsilon$-benzyloxycarbonyllysyl)-Lys$^9$ derivative [(Ac=Boc-Lys(Z)] is obtained with 49 mg of Boc-Lys(Z)-p-nitrophenyl ester.

| TLC: | [CHCl$_3$/CH$_3$OH (8:2)] | $R_f$: 0.55 |
|---|---|---|

EXAMPLE 3

Asn—Phe—Phe—(D-Trp)—Lys(Ac)—Thr—Phe—Gaba (Ac = Gly)

After the addition of 10 mg of palladium-on-carbon (10%) a solution 78 mg of

Asn—Phe—Phe—(D-Trp)—Lys(Z—Gly)—Thr—Phe—Gaba (see Example 2a) in 10 ml of methanol and 0.5 ml of 1 N aqueous acetic acid is hydrogenated for 10 hours at room temperature and normal pressure. For working up, the catalyst is filtered off, the filtrate is concentrated by evaporation in vacuo and the residue is dissolved in 20 ml of tert.-butanol and lyophilised.

The corresponding N$^\epsilon$-leucyl-(Ac=Leu), N$^\epsilon$-phenylalanyl- (Ac=Phe), N$^\epsilon$-prolyl- (Ac=Pro) and N$^\epsilon$-(N$^\alpha$-tert.-butoxycarbonyl)lysyl derivative (Ac=-Boc-Lys) is manufactured in analogous manner:

| TLC: (silica gel): System | R$_f$[Ac=Gly] | R$_f$[Ac=Leu] | R$_f$[Ac=Phe] | R$_f$[Ac=Pro] | R$_f$[Ac=BocLys] |
|---|---|---|---|---|---|
| 101 | 0.60 | 0.69 | 0.71 | — | — |
| 111B | 0.62 | 0.80 | 0.80 | — | — |
| 112A | 0.58 | 0.70 | 0.82 | — | — |
| 151 | 0.59 | 0.70 | 0.70 | — | — |
| 157 | — | — | — | — | 0.65 |
| 157C | — | — | — | 0.73 | — |

The last-named N$^\epsilon$-(N$^\alpha$-tert.-butoxycarbonyl)lysyl derivative (Ac=Boc-Lys) is converted further to form the corresponding peptide having the lysyl radical free, that is to say, to form the

[D-Trp$^8$-N$^\epsilon$-lysyl-Lys$^9$-Gaba$^{12}$]cyclosomatostatin(-5-12)octapeptide of the formula ⌞ Asn—Phe—Phe—(D-Trp)—Lys(Lys)—Thr—Phe—Gaba ⌟ in the following manner:
100 mg of

⌞ Asn—Phe—Phe—(D-Trp)—Lys(Boc—Lys)—Thr—Phe—Gaba ⌟ are dissolved at 5°, under nitrogen, in 1.9 ml of a mixture of 89% by volume of trifluoroacetic acid, 10% by volume of water and 1% by volume of thioglycolic acid, the solution is immediately heated to 25° and left to stand under nitrogen for 25 minutes at room temperature. The product is precipitated with 20 ml of ether and lyophilised from tert.-butanol.

| TLC: | System 101 | R$_f$ 0.55 |
|---|---|---|

EXAMPLE 4

[D-Trp$^8$-N$^\epsilon$-octanoyl-Lys$^9$-Gaba$^{12}$]cyclosomatostatin(5-12)-octapeptide ⌞ Asn—Phe—Phe—(D-Trp)—Lys(Ac)—Thr—Phe—Gaba ⌟

[Ac = CH$_3$(CH$_2$)$_{16}$CO—]

10 μl of triethylamine and 23 mg of caprylic acid anhydride (octanoic acid anhydride) are added to 69 mg of ⌞ Asn—Phe—Phe—(D-Trp)—Lys—Thr—Phe—Gaba ⌟

(in the form of the acetate) in 0.25 ml of dimethylformamide and the mixture is left for 15 hours at room temperature. The product, precipitated with water, is subsequently filtered in chloroform/methanol (1:1) over a column of Sephadex LH-20 ® for purification. The fractions that are pure according to TLC are isolated.

| TLC: [chloroform/methanol/water/glacial acetic acid (90:10:1:0.5)] | R$_f$ 0.23 |
|---|---|

EXAMPLE 5

[D-Trp$^8$-N$^\epsilon$-stearoyl-Lys$^9$-Gaba$^{12}$]cyclosomatostatin(5-12)-octapeptide ⌞ Asn—Phe—Phe—(D-Trp)—Lys(Ac)—Thr—Phe—Gaba ⌟

A solution of 66 mg of

⌞ Asn—Phe—Phe—(D-Trp)—Lys—Thr—Phe—Gaba ⌟

(in the form of the acetate), 26 mg of stearic acid p-nitrophenyl ester and 9 μl of triethylamine in 0.2 ml of dimethylformamide is left overnight at room temperature. The material, precipitated with water, is subsequently filtered in chloroform/methanol (1:1) over a column of Sephadex LH-20 ® and the fractions that are pure according to TLC are isolated.

| TLC: [chloroform/methanol/water/glacial acetic acid (75:26:5:0.5)] | R$_f$ 0.18 |
|---|---|

EXAMPLE 6

[D-Trp$^8$-n$^\epsilon$-(β-carboxypropionyl)-Lys$^9$-Gaba$^{12}$]cyclosomatostatin(5-12)octapeptide ⌞ Asn—Phe—Phe—(D-Trp)—Lys(Ac)—Thr—Phe—Gaba ⌟

(Ac = HOOC—CH$_2$CH$_2$—CO—)

100 g of

⌞ Asn—Phe—Phe—(D-Trp)—Lys—Thr—Phe—Gaba ⌟

(in the form of the acetate) are dissolved in 0.8 ml of dimethylformamide, and 9 μl of N-methylmorpholine and 8.2 mg of succinic acid anhydride are added thereto. After a reaction period of 1 hour at room temperature, 5 ml of (peroxide-free) ether are added. For purification, the oily crude product that precipitates out is triturated with 5 ml of ether, dissolved in 5 ml of tert.-butanol and lyophilised.

| TLC: | [n-butanol/acetic acid/water (3:1:1)] | $R_f$ 0.65 |
| --- | --- | --- |
| | System 52 | $R_f$ 0.63 |
| | System 104 | $R_f$ 0.60 |
| | System 111B | $R_f$ 0.50 |
| | System 157E | $R_f$ 0.58 |

EXAMPLE 7

[D-Trp$^8$—N$^\epsilon$—acetyl-Lys$^9$—Gaba$^{12}$]cyclosomatostatin(5–12)octapeptide

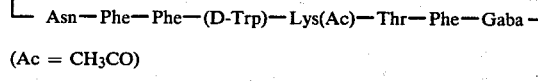

Asn—Phe—Phe—(D-Trp)—Lys(Ac)—Thr—Phe—Gaba (Ac = CH$_3$CO)

A solution of 283 mg of crude H—Asn—Phe—Phe—(D—Trp)—Lys(Ac)—Thr(But)—Phe—Gaba—OH (stage 7.7), 324 mg of N-hydroxybenzotriazole and 495 mg of DCCI in 240 ml of dimethylformamide is kept at 50° for 20 hours. For working up, the solvent is evaporated off in a high vacuum at approximately 30° and the residue is triturated with 10 ml of ethyl acetate. The dicyclohexylurea that precipitates out is filtered off, the filtrate is diluted with ethyl acetate to 50 ml, washed three times using 20 ml of 1 N aqueous oxalic acid each time and then washed with water until neutral, dried over sodium sulphate and concentrated by evaporation in vacuo. For purification, the crude product is subjected to countercurrent distribution in the system methanol/water/chloroform/carbon tetrachloride (2700:675:900:1575 parts by volume) over 430 stages. The phases (K=1.16) that are contained in elements 210 to 254 are combined and concentrated by evaporation in vacuo. The residue is dissolved in 20 ml of tert.-butanol and lyophilised, resulting in a material that is uniform according to thin-layer chromatography and has the formula

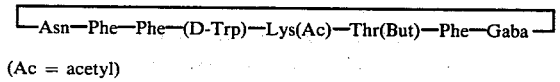

Asn—Phe—Phe—(D-Trp)—Lys(Ac)—Thr(But)—Phe—Gaba (Ac = acetyl)

| TLC: | [chloroform/methanol | (85:15)] | $R_f$ 0.15 |
| --- | --- | --- | --- |
| | [chloroform/methanol/water | (14:6:1)] | $R_f$ 0.70 |

This protected cyclopeptide (186 mg) is dissolved at 5°, under N$_2$, in 1.5 ml of a mixture of 89% by volume of trifluoroacetic acid, 10% by volume of water and 1% by volume of thioglycolic acid, the solution is immediately heated to 25° and, after 90 minutes at room temperature under N$_2$, is precipitated with 15 ml of ether. The resulting crude product is lyophilised from tert.-butanol.

The title compound obtained is identical, according to TLC using three systems, to the product of Example 2.

The linear octapeptide used as starting material is obtained as follows:

STAGE 7.1

Z—(D—Trp)—Lys(Ac)—OH

A solution of 21.87 g of DCCI in 100 ml of acetonitrile is added dropwise at 0° to 5°, over a period of 45 minutes, to a solution of 33.84 g of Z—(D—Trp)—OH and 17.42 g of 8-hydroxyquinoline in 50 ml of acetonitrile. After a further 30 minutes at 5°, the dicyclohexylurea that precipitates out is removed by filtration and washing out with 50 ml of acetonitrile. A solution of 20.70 g of H—Lys(Ac)—OH in 25.9 ml of 4.25 N potassium hydroxide solution and 80 ml of acetonitrile is added to the filtrate and the mixture is left to stand for 15 hours at room temperature. For working up, the reaction mixture is concentrated by evaporation in vacuo and the residue is taken up in 1 liter of ethyl acetate, washed three times using 200 ml of 1 N hydrochloric acid each time at 0° and three times using 200 ml of water each time, the organic phase is dried over sodium sulphate and concentrated by evaporation in vacuo. The resulting brown oil is dissolved in 150 ml of chloroform and, while stirring vigorously, is introduced dropwise into 1.5 liter of hexane. The flocculent, glutinous precipitate is filtered off, washed with 500 ml of hexane and dried in vacuo. For further purification, the material is dissolved in 150 ml of carbon tetrachloride/ethyl acetate (6:4 parts by volume) and is chromatographed with this solvent mixture over a silica gel column. Suitable fractions that are uniform according to thin-layer chromatography are concentrated by evaporation in vacuo, yielding the pure product in the form of a foamlike substance.

| TLC: | [chloroform/methanol/water (14:6:1)] | $R_f$ 0.45 |
| --- | --- | --- |

STAGE 7.2

Z—(D—Trp)—Lys(Ac)—Thr(But)—Phe—OTmse

At 5°, 2.28 g of N-hydroxybenzotriazole and 3.38 g of DCCI are added to a solution of 7.24 g of crude (87% according to titration) H—Thr(But)—Phe—OTmse and 7.58 g of Z—(D—Trp)—Lys(Ac)—OH (stage 7.1) in 100 ml of dimethylformamide and the reaction mixture is kept at 5° for 1 hour and at room temperature for a further 15 hours. For working up, the dicyclohexylurea that precipitates out is filtered off and the filtrate is concentrated by evaporation in a high vacuum. The residue is reprecipitated twice from ethyl acetate/petroleum ether and dried in vacuo.

| TLC: | [chloroform/ethyl acetate (1:1)] | $R_f$ 0.18 |
| --- | --- | --- |
| | [toluene/acetone (1:1)] | $R_f$ 0.50 |

STAGE 7.3

H—(D—Trp)—Lys(Ac)—Thr(But)—Phe—OTmse

After the addition of 0.50 g of palladium-on-carbon (10%) a solution of 5.00 g of Z—(D—Trp)—Lys(Ac)—Thr(But)—Phe—OTmse (stage 7.2) in 300 ml of methanol is hydrogenated for 5 hours at room temperature and normal pressure. For working up, the catalyst is filtered off and, after the filtrate has been concentrated by evaporation, the residue that remains is used immediately in stage 7.4.

STAGE 7.4

Z—Asn—Phe—Phe—(D—Trp)—Lys(Ac)—Thr(But)—Phe—OTmse 210 mg of N-hydroxybenzotriazole and 276 mg of DCCI are added to a solution of 632 mg of Z—Asn—Phe—Phe—OH and 803 mg of H—(D—Trp)—Lys(Ac)—Thr(But)—Phe—OTmse (stage 7.3) in 5 ml of dimethylformamide and the mixture is left for 15 hours at room temperature. For working up, the dicyclohexylurea that precipitates out is filtered off and the filtrate is concentrated by evaporation in a high vacuum. The oily residue is triturated with 5 ml of methanol and filtered by suction. For purification, the undissolved material is again triturated with 5 ml of methanol at 50°, filtered with suction, washed with methanol and dried in vacuo. The product is uniform according to thin-layer chromatography.

| TLC: | [chloroform/methanol (85:15)] | $R_f$ 0.78 |
|---|---|---|
|  | [chloroform/methanol/water (14:6:1)] | $R_f$ 0.82 |

STAGE 7.5

Z—Asn—Phe—Phe—(D—Trp)—Lys(Ac)—Thr(But-)—Phe—OH 900 mg of Z—Asn—Phe—Phe (D—Trp)—Lys(Ac)—Thr(But)—Phe—OTmse (stage 7.4) are dissolved in 23 ml of a freshly prepared anhydrous 0.15 N tetraethylammonium fluoride solution in dimethylformamide and the mixture is kept at 25° for 30 minutes. After cooling to 5°, 0.68 ml of 1 N aqueous hydrochloric acid are added to the reaction mixture, while stirring well, and the product is precipitated by the addition of 70 ml of water. The material filtered off is washed with 5 ml of water, dried in vacuo over phosphorus pentoxide and used directly in stage 7.6.

STAGE 7.6

Z—Asn—Phe—Phe—(D—Trp)—Lys(Ac)—Thr(But-)—Phe—Gaba—OBzl 61 ml of 1-hydroxybenzotriazole and 93 mg of DCCI are added to a mixture of 411 mg of Z—Asn—Phe—Phe—(D—Trp)—Lys(Ac)—Thr(But)—Phe—OH (stage 7.5) and 82 mg of Gababenzyl ester p-toluenesulphonate in 2 ml of dimethylformamide and the mixture is left for 20 hours at room temperature. For working up, 15 ml of ice-cold methanol are added to the mixture and the mixture is filtered. For further purification the solid obtained is stirred for 10 minutes with 5 ml of warm methanol, the suspension is cooled to 0°, and the pure product is filtered off and dried in vacuo.

| TLC: | [chloroform/methanol (85:15)] | $R_f$ 0.75 |
|---|---|---|

STAGE 7.7

H—Asn—Phe—Phe—(D—Trp)—Lys(Ac)—Thr(But-)—Phe—Gaba—OH

After the addition of 50 mg of palladium-on-carbon (10%), a solution of 400 mg of Z—Asn—Phe—Phe—(-D—Trp)—Lys(Ac)—Thr(But)—Phe—Gaba—OBzl (stage 7.6) in 25 ml of dimethylformamide is hydrogenated for 6 hours at room temperature and normal pressure. For working up, after filtering off the catalyst, the solution is concentrated to 2 ml in a high vacuum and the product is precipitated with 25 ml of peroxide-free ether, filtered off and dried in vacuo. The crude product is subjected to the final stage (cyclisation) without further purification.

We claim:

1. An acylpeptide of the formula

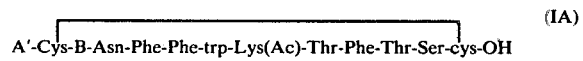

A'-Cys-B-Asn-Phe-Phe-trp-Lys(Ac)-Thr-Phe-Thr-Ser-cys-OH (IA)

in which
A' represents H—Ala—Gly—, Ac—Ala—Gly, H— or Ac—,
B represents Lys, Lys(Ac) or Lys(X) (wherein X is an ε-amino-protecting group),
trp represents L-Trp, D-Trp or an analogous radical, which carries in the indole nucleus a halogen atom,
cys represents L-Cys or D-Cys and
Ac represents an acyl radical of an optionally substituted alkanecarboxylic acid, present at the free amino group,
and non-toxic salts and pharmacologically acceptable complexes thereof.

2. An acylpeptide of the formula

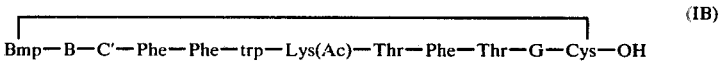

Bmp—B—C'—Phe—Phe—trp—Lys(Ac)—Thr—Phe—Thr—G—Cys—OH (IB)

in which
Bmp represents the desaminocysteine residue,
B represents Lys, Lys(Ac) or Lys(X) (wherein X is an ε-amino-protecting group),
C' represents Asn or His,
trp represents L-Trp, D-Trp or an analogous radical, which carries in the indole nucleus a halogen atom,
G represents L-Ser, D-Ser or the residue of a secondary α-amino acid having a maximum of 8 carbon atoms, and
Ac represents an acyl radical of an optionally substituted alkanecarboxylic acid, present at the free amino group,
and non-toxic salts and pharmacologically acceptable complexes thereof.

3. An acylpeptide of the formula

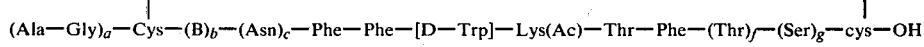

(Ala—Gly)$_a$—Cys—(B)$_b$—(Asn)$_c$—Phe—Phe—[D—Trp]—Lys(Ac)—Thr—Phe—(Thr)$_f$—(Ser)$_g$—cys—OH (IC)

in which
cys represents L-Cys or D-Cys,
B represents Lys, Lys(Ac) or Lys(X) (wherein X is an ε-amino-protecting group),
Ac represents an acyl radical of an optionally substituted alkanecarboxylic acid, present at the free amino group, and
a,b,c,f and g each represents, independently of one another, 0 or 1, and non-toxic salts and pharmacologically acceptable complexes thereof.

4. An acylpeptide of the formula

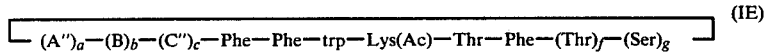

in which
- trp represents L-Trp, D-Trp or an analogous radical, which carries in the indole nucleus a halogen atom, and
- Ac represents an acyl radical of an optionally substituted alkanecarboxylic acid, present at the free amino group, and non-toxic salts and pharmacologically acceptable complexes thereof.

5. An acylpeptide of the formula

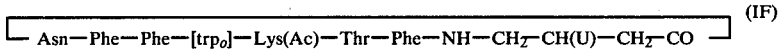

in which
- A" denotes the residue of an ω-amino-lower alkanecarboxylic acid of the partial formula —NH—CH(R)—(CH$_2$)$_n$—CO— (wherein n represents 0 or an integer from 1 to 6 and R represents hydrogen or carboxyl) which, if n=2 and R is hydrogen, can also be substituted by a cyclic hydrocarbyl radical and, in that case, is designated by the symbol Gaba(Ar),
- B represents Lys, Lys(Ac) or Lys(X) (wherein X is an ε-amino-protecting group),
- C" represents Asn or Ala,
- trp represents L-Trp, D-Trp or an analogous radical, which carries in the indole nucleus a halogen atom,
- Ac represents an acyl radical of an optionally substituted alkanecarboxylic acid, present at the free amino group, and
- a,b,c,f and g each represents, independently of one another, 0 or 1, and non-toxic salts and pharmacologically acceptable complexes thereof.

6. An acylpeptide according to claim 5, in which Ac represents an acyl radical of an optionally substituted alkanecarboxylic acid, present at the free amino group, trp represents D-Trp, A" denotes an ω-amino-lower alkanecarboxylic acid residue, in which R represents hydrogen and n represents 0 or an integer from 1 to 3, B represents Lys, Lys(Ac) or Lys(INOC) and C" represents Asn or Ala, and f and at least one of the symbols a, b, c and g are equal to 1, whilst the others each represent independently of one another, 0 or 1.

7. An acylpeptide according to claim 5, in which Ac represents an acyl radical of an optionally substituted alkanecarboxylic acid, present at the free amino group, trp represents D-Trp, A" represents a radical Gaba(Ar) having the hydrocarbyl Ar in the β-position, or the ω-amino-lower alkylcarboxylic acid residue, C" represents Ala or Asn, a equals 1, c equals 0 or 1 and b, f and g equal 0.

8. An acylpeptide according to claim 7, in which A" represents the radical —NH—CH(R)—(CH$_2$)$_n$—CO, in which n=5 and R is hydrogen or carboxyl, a equals 1, and b, c, f and g all equal 0, and the other radicals have the meanings given in claim 7.

9. An acylpeptide of the formula

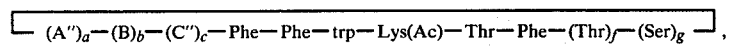

in which trp$_0$ represents D-Trp or D-(5F)Trp, Ac represents an acyl radical of an optionally substituted alkanecarboxylic acid, present at the free amino group, and U represents hydrogen or an optionally substituted cyclic hydrocarbyl radical Ar.

10. An acylpeptide according to claim 9, in which U represents hydrogen and the other symbols have the meanings given in claim 9.

11. An acylpeptide according to claim 9, in which U represents the phenyl, cyclohexyl, 2-naphthyl, 1-naphthyl or 3-phenoxyphenyl radical and the other symbols have the meanings given in claim 9.

12. An acylpeptide according to claim 9 in which Ac represents the radical of an alkanemonocarboxylic acid having a maximum of 18 carbon atoms or an alkanedicarboxylic acid having a maximum of 9 carbon atoms.

13. An acylpeptide according to claim 9, in which Ac represents the residue of a naturally occurring α-amino acid or a closely related analogue thereof.

14. An acylpeptide according to claim 9 of the formula IF, in which trp$_0$ represents D-Trp, U represents hydrogen and Ac represents glycyl, leucyl or phenylalanyl.

15. An acylpeptide according to claim 9 of the formula IF, in which trp$_0$ represents D-Trp, U represents hydrogen and Ac represents prolyl.

16. An acylpeptide according to claim 9 of the formula IF, in which trp$_0$ represents D-Trp, U represents hydrogen and Ac represents N$^\alpha$-tert.-butoxycarbonyllysyl or lysyl.

17. A pharmaceutical preparation for the treatment of diabetes and/or gastrointestinal bleeding in humans and mammals, containing an effective amount of at least one acylpeptide defined an any one of claims 9 or 1–5.

18. A therapeutic method for the treatment of diabetes and/or gastrointestinal bleeding in humans and mammals by administration of an effective amount of a acylpeptide defined in any one of claim 9 or 1–5, or in the form of a pharmaceutical preparation containing said acylpeptide.

* * * * *